United States Patent
Shah

(10) Patent No.: US 9,335,246 B2
(45) Date of Patent: May 10, 2016

(54) METHODS FOR DETECTING COINCIDENT SAMPLE EVENTS, AND DEVICES AND SYSTEMS RELATED THERETO

(71) Applicant: Abbott Laboratories, Abbott Park, IL (US)

(72) Inventor: Amish Shah, Pleasanton, CA (US)

(73) Assignee: Abott Laboratories, Abott Park, IL (US)

( * ) Notice: Subject to any disclaimer, the term of this patent is extended or adjusted under 35 U.S.C. 154(b) by 227 days.

(21) Appl. No.: 14/137,363

(22) Filed: Dec. 20, 2013

(65) Prior Publication Data

US 2014/0268102 A1 Sep. 18, 2014

Related U.S. Application Data

(60) Provisional application No. 61/785,301, filed on Mar. 14, 2013.

(51) Int. Cl.
*G01N 15/14* (2006.01)
*G01N 15/10* (2006.01)

(52) U.S. Cl.
CPC ........ *G01N 15/1429* (2013.01); *G01N 15/1459* (2013.01); *G01N 2015/1006* (2013.01); *G01N 2015/1461* (2013.01); *G01N 2015/1486* (2013.01)

(58) Field of Classification Search
None
See application file for complete search history.

(56) References Cited

U.S. PATENT DOCUMENTS

| | | | | |
|---|---|---|---|---|
| 3,949,198 | A * | 4/1976 | Coulter | G01N 15/1227 377/12 |
| 3,987,391 | A * | 10/1976 | Hogg | G01N 15/1227 377/12 |
| 4,510,438 | A * | 4/1985 | Auer | G01N 15/1429 324/71.4 |
| 5,121,443 | A | 6/1992 | Tomlinson | |
| 5,247,461 | A * | 9/1993 | Berg | G01N 15/1031 324/464 |
| 5,452,237 | A * | 9/1995 | Jones, Jr. | G01N 15/1227 702/182 |
| 8,209,128 | B1 | 6/2012 | Gourley | |
| 9,261,515 | B2 * | 2/2016 | Vacca | G01N 33/721 |
| 2007/0143033 | A1 * | 6/2007 | Zhang | G01N 15/12 702/26 |
| 2008/0268469 | A1 | 10/2008 | Srienc et al. | |
| 2010/0090677 | A1 * | 4/2010 | Britton | G01N 15/1429 324/71.1 |

* cited by examiner

*Primary Examiner* — Gordon J Stock, Jr.
(74) *Attorney, Agent, or Firm* — Edward J. Baba; Brian E. Davy; Bozicevic, Field & Francis LLP

(57) ABSTRACT

In some aspects of the present disclosure, methods of detecting coincident sample events are provided. The methods include receiving a first set of signal data representing detected signals from a flow cytometer system; detecting, with a peak detection module, one or more peaks within the signal data; and cancelling, with a successive cancellation module, one or more individual sample events from the signal data at corresponding time indexes, wherein the cancellation of more than one individual sample event is successive. Devices and system related thereto are also provided.

37 Claims, 7 Drawing Sheets

METHODS FOR DETECTING COINCIDENT SAMPLE EVENTS, AND DEVICES AND SYSTEMS RELATED THERETO

CROSS-REFERENCE

This application claims the benefit of U.S. Provisional Patent Application No. 61/785,301 filed Mar. 14, 2013, which application is incorporated herein by reference in its entirety.

SUMMARY

In some aspects of the present disclosure, methods of detecting coincident sample events are provided. The methods include receiving a first set of signal data representing detected signals from a flow cytometer system; detecting, with a peak detection module, one or more peaks within the signal data; and cancelling, with a successive cancellation module, one or more individual sample events from the signal data at corresponding time indexes, wherein the cancellation of more than one individual sample event is successive.

In some aspects of the present disclosure, flow cytometer systems are provided. The flow cytometer systems include a flow cell for streaming a hydro-dynamically focused core stream past an interrogation zone; beam shaping optics positioned to receive and manipulate a first light beam, and to produce a resulting light beam that irradiates the core stream at the interrogation zone of the flow cell; a detection system to detect resulting light from the flow cell when irradiated; and a data processing system operably coupled to the detection system to generate and process signal data representing the resulting light detected by the detection system. The processing of the signal data includes receiving a first set of signal data from the detection system; detecting one or more peaks within the signal data; and cancelling one or more individual sample events from the signal data at corresponding time indexes, wherein the cancellation of more than one individual sample event is successive.

In some aspects of the present disclosure, non-transient machine-readable mediums are provided. The machine readable mediums have machine-executable instructions stored thereon, which when executed by one or more processing devices, cause the one or more processing devices to receive a first set of signal data representing detected signals from a flow cytometer system; detect, with a peak detection module, one or more peaks within the signal data; and cancel, with a successive cancellation module, one or more individual sample events from the signal data at corresponding time indexes, wherein the cancellation of more than one individual sample event is successive.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the systems and methods presented. In the drawings, like reference numbers indicate identical or functionally similar elements.

DETAILED DESCRIPTION

Figure 1:
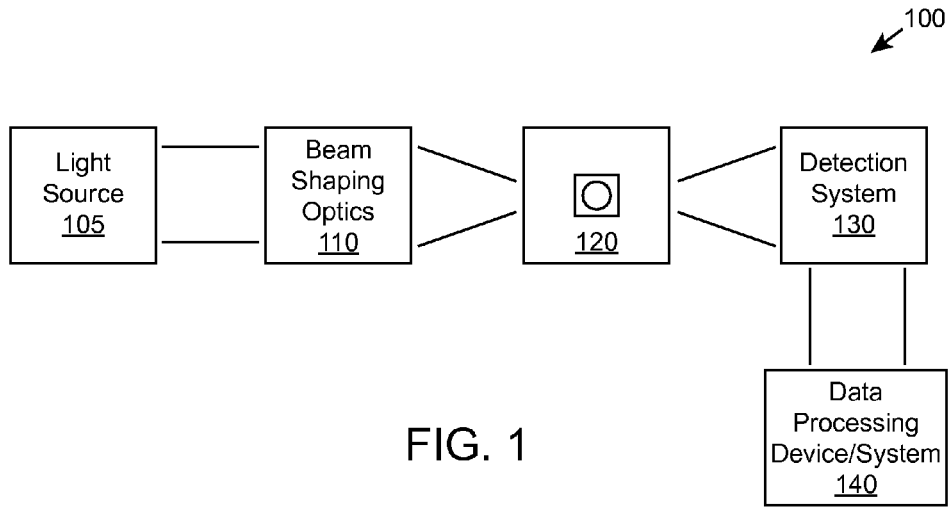
FIG. 1 illustrates a flow cytometer system, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Unless defined otherwise, all technical and scientific terms used herein have the same meaning as commonly understood by one of ordinary skill in the art to which this invention belongs.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In some aspects, the methods, devices, and systems of the present disclosure relate to sample detection in flow cytometers. The specific sample may vary depending on application and may include, but is not limited to, cells, particles, or combinations thereof. For example, in certain embodiments, the sample may include one or more of the following: red blood cells (RBC), white blood cells (WBC), and platelets (PLC). The systems and methods may relate to various types of processing of the samples, such as identification of the samples, differentiation of the samples, counting of the sample, etc.

The term "event" is used herein to refer generally to one or more samples (e.g., cells and/or particles) passing through the interrogation zone of a flow cell and being irradiated by a light source (e.g., laser beam). The event generates a resulting light signal that is detected by a detection system. The resulting light signal may include many different detected parameters such as, but not limited to, axial light loss, scattered light, fluorescence, etc. All of the parameters make up what is referred to herein as the "profile of the event".

The term "signal event", "incoming signal event", "signal data" are used herein to refer generally to the resulting energy detected when one or more samples pass through the interrogation zone of a flow cell being irradiated by a light source (e.g., laser beam). The signal event may include one or more sample events. The term "sample event" is used herein to refer generally to the resulting energy of a single sample passing through the interrogation zone and producing parameters that make up the "sample event profile" for that sample event.

In some instances, two or more sample may pass through the interrogation zone of the flow cell while being proximate to one another. The term "coincident event" and "coincident sample event" are used herein to refer generally to the occurrence of two samples (e.g., cells, particles, etc.) passing through the interrogation zone while being proximate to one another. The resulting "event profile" for the resulting signal will have overlapping "sample event profiles".

In some aspects, the methods, devices, and systems of the present disclosure relate to detecting sample events, and identifying and resolving coincident sample events, such as those occurring within a flow cell of a hematology analyzer for example.

In some aspects, the methods, devices, and systems detect precise peak heights and sample event profiles (e.g., area under the pulse, pulse width, and higher order moments) during coincidence sample events. The system and methods provided herein enable a more precise detection of coincident sample events, such as sample events that are proximate to one another and/or smaller sample events that are close to larger sample events. By computing precise peak heights and sample event profiles within the coincidence event, assays may be run with higher concentrations (i.e., less diluted). For instance, certain assays in an analyzer may need to be highly diluted to find the correct count of each cell and/or particle as well as ratio between the two counts—e.g., a Retic assay to find the percentage ratio between RBC and Reticulocyte. Capturing sample events at a higher resolution permits more coincident events to pass through the flow cell, and enables assays to run for shorter times while still maintaining high statistical accuracy and higher precision of the sample event parameters, which effectively increases throughput. Samples can be processed at a faster rate—e.g., 1.5 to 2 times faster, and greater. The systems and methods described herein enable precision with higher concentrated sample levels than with those resulting from statistical correction. Furthermore, the higher concentration samples use less sheath consumption and less waste.

As summarized above, in some aspects of the present disclosure, methods of detecting coincident sample events are provided. The methods include receiving a first set of signal data representing detected signals from a flow cytometer system; detecting, with a peak detection module, one or more peaks within the signal data; and cancelling, with a successive cancellation module, one or more individual sample events from the signal data at corresponding time indexes, wherein the cancellation of more than one individual sample event is successive.

As summarized above, in some aspects of the present disclosure, flow cytometer systems are provided. The flow cytometer systems include a flow cell for streaming a hydro-dynamically focused core stream past an interrogation zone; beam shaping optics positioned to receive and manipulate a first light beam, and to produce a resulting light beam that irradiates the core stream at the interrogation zone of the flow cell; a detection system to detect resulting light from the flow cell when irradiated; and a data processing system operably coupled to the detection system to generate and process signal data representing the resulting light detected by the detection system. The processing of the signal data includes receiving a first set of signal data from the detection system; detecting one or more peaks within the signal data; and cancelling one or more individual sample events from the signal data at corresponding time indexes, wherein the cancellation of more than one individual sample event is successive.

As summarized above, in some aspects of the present disclosure, non-transient machine-readable mediums are provided. The machine readable mediums have machine-executable instructions stored thereon, which when executed by one or more processing devices, cause the one or more processing devices to receive a first set of signal data representing detected signals from a flow cytometer system; detect, with a peak detection module, one or more peaks within the signal data; and cancel, with a successive cancellation module, one or more individual sample events from the signal data at corresponding time indexes, wherein the cancellation of more than one individual sample event is successive.

The following detailed description of the figures refers to the accompanying drawings that illustrate exemplary embodiments. Other embodiments are possible. Modifications may be made to the embodiments described herein without departing from the spirit and scope of the present invention. Therefore, the following detailed description is not meant to be limiting.

FIG. 1 illustrates a top view of a flow cytometer system, according to one embodiment. Flow cytometer system 100 is shown including beam shaping optics 110, flow cell 120, light source 140, detection system 130, and data processing system 140.

Light source 140 may include, for example, a laser coupled to an optical fiber to generate a laser beam directed to the beam shaping optics 110 positioned between the light source 140 and flow cell 120. The laser beam is manipulated by the beam shaping optics 110 to provide a focused beam directed to an interrogation zone of the flow cell 120. A core stream within the flow cell 120 is irradiated by the focused beam as it flows past the interrogation zone of the flow cell 120.

Flow cell 120 is positioned such that the light from the beam shaping optics 110 is directed to an interrogation zone in the flow cell 120. Flow cell 120 includes a core stream which is directed past the interrogation zone of the flow cell 120. In this way, the core stream flowing through the flow cell 120 is irradiated by the focused light as it passes through the interrogation zone. The core stream may include, for example, samples (e.g., particles, cells, or combinations thereof) which are hydro-dynamically focused in a fluid sheath (e.g., injected into the center of the fluid sheath) and directed past the interrogation zone in the flow cell 102.

Detection system 130 is positioned next to the flow cell to detect light emitted from the flow cell. As samples pass through the interrogation zone, the resulting light characteristics, such as light scatter, light loss, fluorescence, etc. For example, detection system 130 may include a photomultiplier tube (PMT), photodiode (PD), etc., for detecting light and converting it to an electrical signal. Detection system 130 may include one or more detectors to detect axial light loss, and/or one or more detectors to measure the amount of scattered light resulting when the core stream is irradiated at the interrogation zone. For instance, the detection system 130 may include one or more detectors to detect intermediate angle scatter (IAS) and/or forward scatter. The detection system 130 may also include lenses and detectors for detecting fluorescent light, polarized side scatter, and/or depolarized side scatter. Furthermore, one or more detectors may be positioned in various positions around the flow cell—e.g., at 90 degrees from the flow cell. The detection system 130 may also include other components such as lenses, reflectors or mirrors, etc., which are not shown. For example, detection system 130 may include components such as lenses, reflectors or mirrors, etc.

The light characteristics, resulting from each interrogated sample (e.g., particle or cell), is detected to generate corresponding electrical signals. Data processing system 140 is operably coupled to detection system 130 and receives the corresponding electrical signals. These electrical signals are converted from analog signals to digital signals by an analog-to-digital converter (ADC), for example to generate signal data at a given sampling rate to represent the electrical signals from the detection system 130. In certain embodiments, the analog electrical signals may go through a pre-amplification stage before being converted to digital signals. The term "signal data" is used herein to refer generally to the digital signal generated from sampling the analog signal.

Data processing system 140 may use or otherwise process the signal data to determine various parameters of the sample events (e.g., for sample cells and/or particles). Example sample event parameters that are determined by data processing system 140 may include, but are not limited to, magnitudes of the signal (e.g., signal pulse from a detected event), signal peaks and their respective heights, signal widths, areas under the signal. In certain embodiments, data processing system may determine one or more parameters of higher order moments—e.g., standard deviation of the signal (e.g., second order moment), skewness of the signal (e.g., third order moment), and kurtosis of the signal (e.g., fourth order moment). Other parameters may also be found, such as the Discrete Fourier Transform (DFT). These parameters may then be used for further analysis, such as for cell classification purposes. The data processing system 140 uses one or more of these parameters to identify and resolve coincident events occurring within the flow cell.

Figure 2:
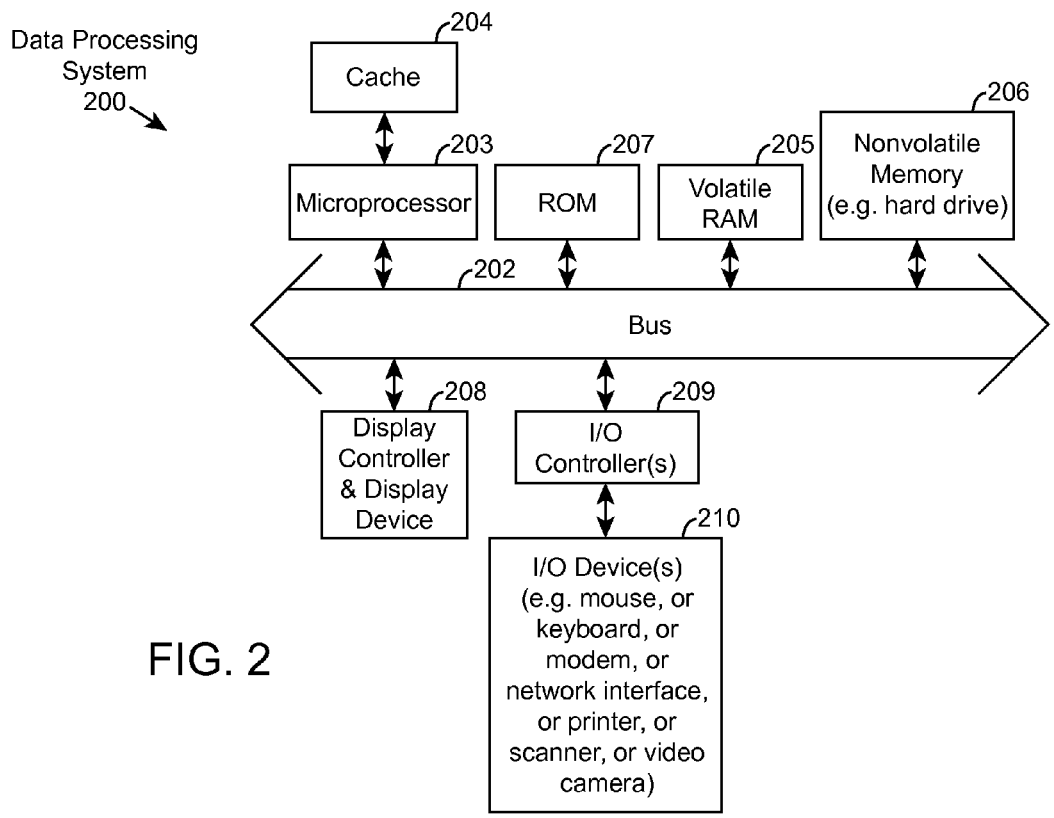
FIG. 2 illustrates a data processing system, according to one embodiment.

FIG. 2 illustrates an example block diagram of a data processing system upon which the disclosed embodiments may be implemented. Embodiments of the present invention may be practiced with various computer system configurations such as hand-held devices, microprocessor systems, microprocessor-based or programmable user electronics, minicomputers, mainframe computers and the like. The embodiments can also be practiced in distributed computing environments where tasks are performed by remote processing devices that are linked through a wire-based or wireless network. FIG. 2 shows one example of a data processing system, such as data processing system 200, which may be used with the present described embodiments. Note that while FIG. 2 illustrates various components of a data processing system, it is not intended to represent any particular architecture or manner of interconnecting the components as such details are not germane to the techniques described herein. It will also be appreciated that network computers and other data processing systems which have fewer components or perhaps more components may also be used. The data processing system of FIG. 2 may, for example, be a personal computer (PC), workstation, tablet, smartphone or other hand-held wireless device, or any device having similar functionality. Furthermore, the term "data processing system" may also encompass programmable circuitry programmed or configured by software and/or firmware, or within special-purpose "hardwired" circuitry, or a combination of such forms. Such special-purpose circuitry (if any) can be in the form of, for example, one or more application-specific integrated circuits (ASICS), programmable logic devices (PLDs), field-programmable gate arrays (FPGAs), etc. For example, the data processing device may be in the form of a FPGA including a various modules operably and communicably coupled to one another. For instance, the FPGA may include a module functioning as a processing device, a module functioning as memory, a base line restoration module, a peak detection module, a successive cancellation module, a channel analysis module, etc.

For the example embodiment shown in FIG. 2, the data processing system 201 includes a system bus 202 which is coupled to a microprocessor 203, a Read-Only Memory (ROM) 207, a volatile Random Access Memory (RAM) 205, as well as other nonvolatile memory 206. In the illustrated embodiment, microprocessor 203 is coupled to cache memory 204. System bus 202 can be adapted to interconnect these various components together and also interconnect components 203, 207, 205, and 206 to a display controller and display device 208, and to peripheral devices such as input/output ("I/O") devices 210. Types of I/O devices can include keyboards, modems, network interfaces, printers, scanners, video cameras, or other devices well known in the art. In one embodiment, I/O device includes interface for receiving data derived from the detection system 130. In some instances, the signal data received is already converted to a digital signal, and in other instances, the interface includes an analog to digital converter to digitize the incoming signal into the signal data to be processed. I/O devices 210 may in some instances be coupled to the system bus 202 through I/O controllers 209. In one embodiment, the I/O controller 209 includes a Universal Serial Bus ("USB") adapter for controlling USB peripherals or other type of bus adapter.

RAM 205 can be implemented as dynamic RAM ("DRAM") which requires power continually in order to refresh or maintain the data in the memory. The other non-volatile memory 206 can be a magnetic hard drive, magnetic optical drive, optical drive, DVD RAM, or other type of memory system that maintains data after power is removed from the system. While FIG. 2 shows that nonvolatile memory 206 as a local device coupled with the rest of the components in the data processing system, it will be appreciated by skilled artisans that the described techniques may use a nonvolatile memory remote from the system, such as a network storage device coupled with the data processing system through a network interface such as a modem or Ethernet interface (not shown).

Data processing system 140 receives the detected signal from the detection system 130. If the detected signal from the detection system 130 has not be digitized yet, the data processing system 140 digitizes the detected signal—e.g., with an analog-to-digital converter (ADC)—to generate the signal data for processing. The sampling rate of the analog-to-digital converter may vary in different embodiments. In one embodiment, the analog-to-digital converter of the data processing system digitizes the incoming signal from the detection system (e.g., a photomultiplier tube (PMT), photodiode (PD), etc.) at 10 million samples per second (MSPS).

For example, each sample passing through the flow cell interacts with the laser beam and produces a convolution output of a laser beam profile and sample size in the flow-direction. This convolution signal is captured by the detection system (e.g., PMT or PD) and digitized by the ADC. This digitized output is the input signal data for the methods described herein.

The methods may include processing the signal data to find the peak height of the event as well as detecting possible individual sample events within the coincident events. Other parameters may also be determined, such as the pulse width, the area under curve, and other higher order moments which may be computed once the pulse shape of the individual cell profile is extracted from the coincidence event. The methods may also find the peaks of the event even under the noisy signal condition, preventing false detections from electronic or interference noise.

Once a peak of a sample event is detected in the signal data, a model sample event profile is generated from a pre-stored beam profile and the detected peak height of that sample event. If more than one peak heights are detected during the detection process, the energy of the individual sample events are computed based on their peak heights, and the energy of the sample event are subtracted successively from the combined event response at the corresponding time indexes of the peaks. In one embodiment, the signal with maximum peak value is subtracted first from combined (coincident) signal response. The algorithm works successively on leftover signal energy to detect any other smaller sample events within the coincident event until the energy of the leftover signal does not decrease by the amount of the subtracted signal energy.

In one embodiment, the successive cancellation process is also iterative in that it corrects a peak height determination of a previously detected and cancelled sample event. For example, when sample events are close together, the first larger peak height may first be detected and cancelled from the signal data. Next, the second peak is detected for cancellation. The second peak height is detected and the second peak cancelled from the original signal data. Based on the cancellation of the second peak from the original signal data, the first peak height may then be corrected. The successive cancellation process may continue with the second peak being successively cancelled from the remaining signal data after the cancellation of the first peak.

Figure 5:
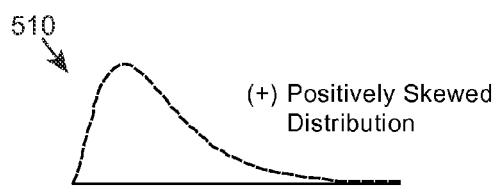
FIG. 5 illustrates an example plot of skewness, according to one embodiment.
Figure 5:
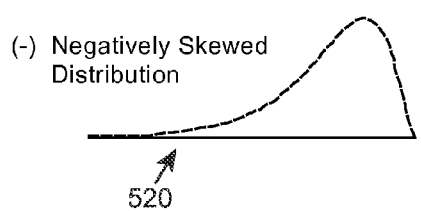
Figure 6:
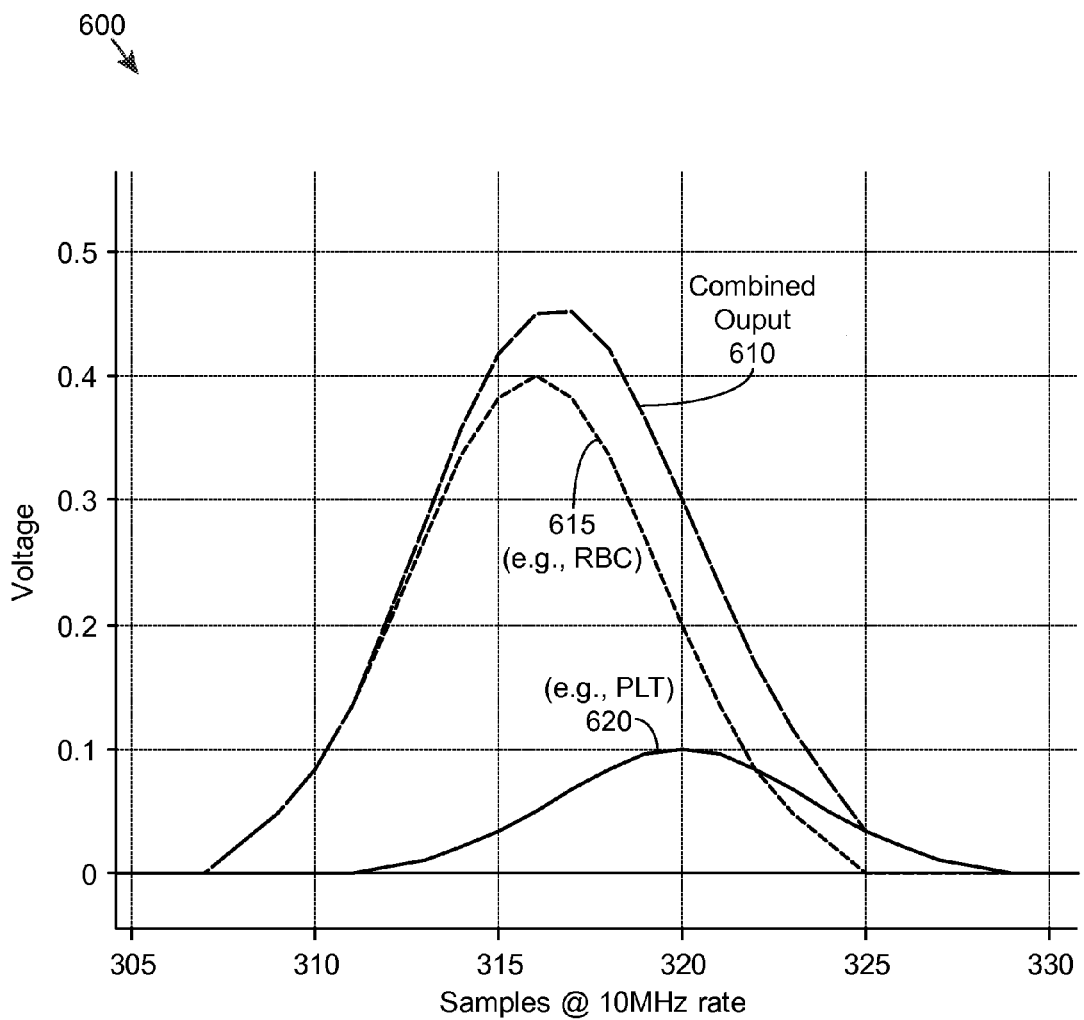
FIG. 6 illustrates a plot of a combined response for a coincident event having a single peak, along with plots of the individual sample events within the coincident event, according to one embodiment.

When only a single peak event is detected, skewness ($3^{rd}$ order moment) may be computed to detect whether there any small sample events riding at the leading or lagging trail of a larger sample event—e.g., as shown in FIGS. 5 and 6. For example, when a Skewness of more than a predetermined threshold (e.g., +/−0.15) is computed, a successive cancellation is initiated to obtain the correct sample event heights and sample event profiles. In one embodiment, the successive cancellation is also iterative as similarly described above.

Figure 3:
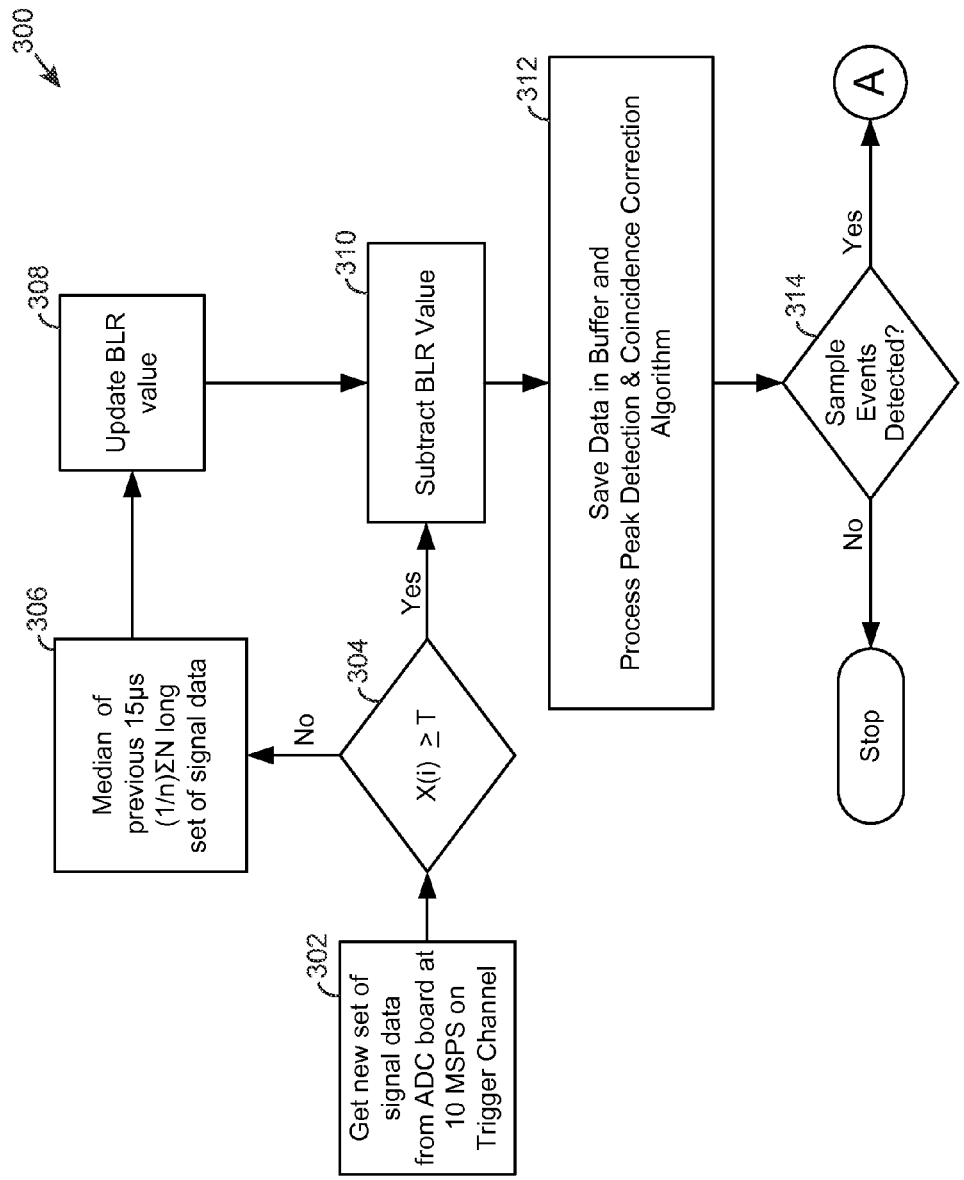
FIG. 3 illustrates a flow chart for detecting coincident sample events, according to one embodiment.
Figure 3:
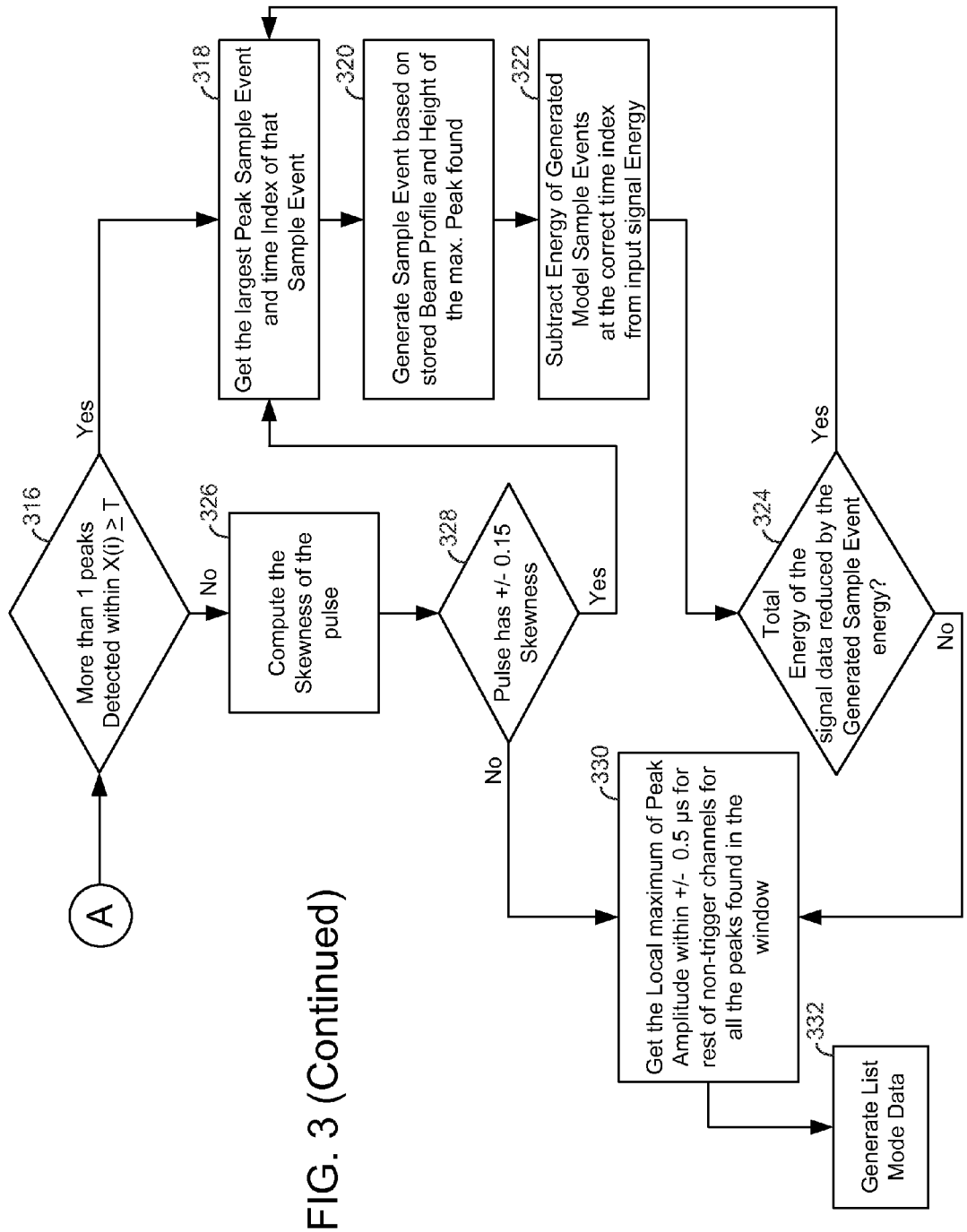

FIG. 3 illustrates a flowchart for a method of detecting coincident sample events, according to one embodiment. Method 300 begins by performing a base line restoration in order to determine the precise height of a sample event ($X_p$). For example, a base line restoration module may receive a set of signal data and perform a base line restoration. The base line restoration provides for a more precise estimation by accounting for system variations and fluctuations, such as those caused by laser optics, electronics, noise, interference, temperature variations, thermal radiations, fluid viscosity, etc.

At block 302, a new set of signal data is obtained—e.g., from an analog-to-digital converter (ADC) coupled to a detection system of a flow cytometer system. A base line restoration value is computed by taking the median value of a previous set of signal data that fall under a predetermined threshold value, T, as represented by blocks 304, 306, and 308. For example, in block 306, the median value is calculated from a 15 microsecond time period of signal data that is under the predetermined threshold, T. For instance, the 15 microsecond time period provides approximately 150 samples at the 10 MHz sampling rate, for instance. It should be appreciated that the time period and sampling rate may vary in different embodiments. The computed median value is used as the base line restoration value, or is used as the updated base line restoration value, as represented by block 308.

The predetermined threshold value represents a threshold value for the indication of one or more sample events has occurred. The predetermined threshold value may be experimentally defined and may vary for different particles or cells being implemented. The threshold for red blood cells (RBC) may be implemented as, but is not limited to, 1.25% of the full dynamic range, for example. The threshold for white blood cells (WBC) may be implemented as, but is not limited to, 6-7% of the full dynamic range, for example. The threshold for Reticulocyte may be implemented as, but is not limited to, 2-3% of the full dynamic range, for example. These example values are exemplary and should not be construed as limiting.

At block 310, the base line restoration is performed by subtracting the updated base line restoration value from block 308 (e.g., the computed median value from block 306) from the incoming signal data, X(i), when the signal data goes above the predetermined threshold value, T, in block 302 and 304. In the embodiment shown, the sampling rate is 10 million samples per second (MSPS). At block 312, the resulting signal data after subtracting the base line restoration value is then used for further processing, such as for peak detection and/or coincidence correction. In some instances, the resulting signal data may be buffered or stored in memory.

Once the base line restoration is performed, a peak detection module detects the peak of the signal event. At block 314, the peak detection module determines whether sample events are detected. In one embodiment, a signal event, which may include one or more sample events, is detected when a peak of the signal pulse increases above the predetermined threshold value. There may also be more than one sample event, as well as more than one peak above the threshold value. Accordingly, the peak detection module identifies peaks of the signal pulse and detects whether they are above the predetermined threshold. In one embodiment, for example, the signal event detection criteria may be as follows:

$X_P \geq T$
$X_p \geq X_{p+1} \geq T$  $X_p \geq X_{p+2} \geq T$  $X_p \geq X_{p+3} \geq T$
$X_p \geq X_{p-1} \geq T$  $X_p \geq X_{p-2} \geq T$  $X_p \geq X_{p-3} \geq T$
$X_p \geq X_{p+4}$  $X_p \geq X_{p+5}$  $X_p \geq X_{p+6}$
$X_p \geq X_{p-4}$  $X_p \geq X_{p-5}$  $X_p \geq X_{p-6}$ where T is a predetermined or programmable threshold value, and $X_{p+n}$ is the $n^{th}$ sample from $X_p$. If the incoming signal data satisfies all of these conditions, then single or multiple peak heights of the signal event may be recorded.

At block 316, the peak detection module determines whether more than one peak is detected within the signal event. If multiple peak heights are detected within the signal event, then it is determined that multiple sample events are closely detected during the time when samples were above the threshold value. A successive cancellation module may then be executed to successively cancel out the energy of individual sample events, as represented by the "Yes" arrow from block 316 to block 320—e.g., to successively subtract out the energy of one sample event at a time. In one embodiment, the cancellation process may also be iterative in that one or more previous peak height determinations from previous cancellations may be corrected based on the cancellation of a successive peak from the original signal data.

In order to measure the precise peak height of each individual sample event within the coincidence, the successive cancellation module subtracts the energy for each sample event individually from the signal data (e.g., the combined input signal for the multiple sample events). In one embodiment, the largest sample events are detected and subtracted first one at a time, to permit clearer detection of smaller sample events within the signal data. For example, white blood sample events may be larger than red blood sample events and platelet events, in which case the white blood sample events would be detected and subtracted out successively first. The detection of the precise peak of the pulse enables the successful detection and cancellation of the stronger signal (e.g., WBC without introducing any residual energy that may cause an error—e.g., by being mistaken as a small sample event. Again, the cancellation process may also be iterative in that one or more previous peak height determinations from previous cancellations may be corrected based on the cancellation of a successive peak from the original signal data.

At block 318, the largest peak sample event and the corresponding time index for the sample event is identified. From the peak information, an ideal waveform of the Gaussian signal may be generated—e.g., based on a stored or predetermined beam profile and the height of the maximum peak found—as represented by block 320.

In one embodiment, the combined input signal (e.g., signal data) is mathematically represented by the sum of convolutions of the laser beam profile and the size of the sample in flow direction, such as represented by the following equation.

$$x(t) = \sum_{i=1}^{N} X_p * h(t) + n(t)$$

where $x(t)$ is the incoming set of signal data; $X_p$ size of the individual sample events in the flow-direction within the incoming set of signal data; $h(t)$ is the laser bean profile; $*$ is the convolution process; and $n(t)$ is the electronics and/or interference noise. Therefore, once the size of the sample event in the flow-direction, $X_p$, is detected, a model sample event, representing an ideal convoluted signal, may be generated from the saved laser beam profile. For instance, in one embodiment, the model sample event (e.g., ideal convoluted signal for that sample event) may be found from the following equation.

$$x_p' = X_p * h(t)$$

The energy from the model sample event (e.g., ideal convoluted signal), $x_p'$, is then subtracted at the correct time index from the energy of the signal data, $x(t)$, as represented block 322. An example equation of the energy of the signal data may be represented as follows.

$$x(t) = x(t) - x_p'$$

At block 324, a determination is made as to whether the total energy of the signal data is reduced by the generated energy of the model cell (e.g., the ideal convoluted sample signal). In other words, whether there is remaining energy left when the energy of the model sample event is subtracted from the energy of the signal data.

If significant leftover energy remains (e.g., the energy of the signal data is reduced by energy of the model sample event), then it is input again for the next successive cancellation to find another equivalently-sized sample event or smaller sample event within the signal data (e.g., combined signal), as represented by the arrow form block 324 back to block 318. For example, at block 318, the largest peak sample event is then detected for the remaining signal data left over from the first cancellation. At block 320, a second model sample event is generated for this peak sample event, and at block 322, the energy from the second model sample event is successively subtracted at the corresponding time index from the remaining sample data left over from the first cancellation. Thereafter, at block 324, a determination is made as to whether the total energy of the signal data is reduced after the cancellation of the first and second cancellations (e.g., whether there is any leftover energy after the first and second cancellation). In one embodiment where the cancellation is iterative, the second generated model sample event is successively subtracted at the corresponding time index from the original signal data, and based on the results of this subtraction, the first peak height (determined for the first sample event that was cancelled) is corrected.

It should be appreciated that the iterative correction may occur for a previous peak height that is not necessarily the immediately preceding peak height that was determined and cancelled. For example, after the cancellation of two peaks, a third peak detected for cancellation may be used to generate a third model sample event for the third peak, and the energy for the third model sample event may be subtracted from the original signal data to correct the peak height determination of the first peak and/or second peak height.

If the energy does not decrease (e.g., if there is no remaining leftover energy or insignificant or negligible leftover energy), for example as represented by the following equation, then it may be determined that all the sample events within that coincident event were detected.

$$x(t) - x_p' \geq x_p'$$

If no leftover energy remains (the total energy of the signal is not reduced), then all the individual sample events within the incoming signal are detected. Once the individual peaks for the incoming signal have been identified with right time index, then it is possible to repeat the same calculations for all the channels. Each channel may represent, for example, detection of various data, such as, but not limited to, side scatter, axial light loss, polarized scatter, depolarized scatter, fluorescence, etc. However, because the individual sample events occur at the same time, the time indexes of each individual peak may be used to find the corresponding features at those times in the other channels. In some instances, a range of time based on the time indexes may be used, such as within a predetermined time before and after the time indexes. This provides an alternative way to obtain the same information from the other channels, rather than performing the same process on the other channels, which may consume more processing power and time. For example, as shown in FIG. 3, the time indexes for each of the individual sample event peaks may be used to find the corresponding features in other channels at those approximate times that the sample events occur. For example, at block 330, a channel analysis module identifies the corresponding features in the other channels (e.g., sample event peaks), by identifying a time range based on the time indexes of the individual sample events detected by the successive cancellation module. For instances, in the embodiment shown, the time range is +/−0.5 microseconds from the time indexes of the individual sample events. Other tolerances, or sizes of the time range, may vary in different embodiments. In this way, sample event profile data from all channels may be gathered for each sample event, as represented by block 132.

Figure 4:
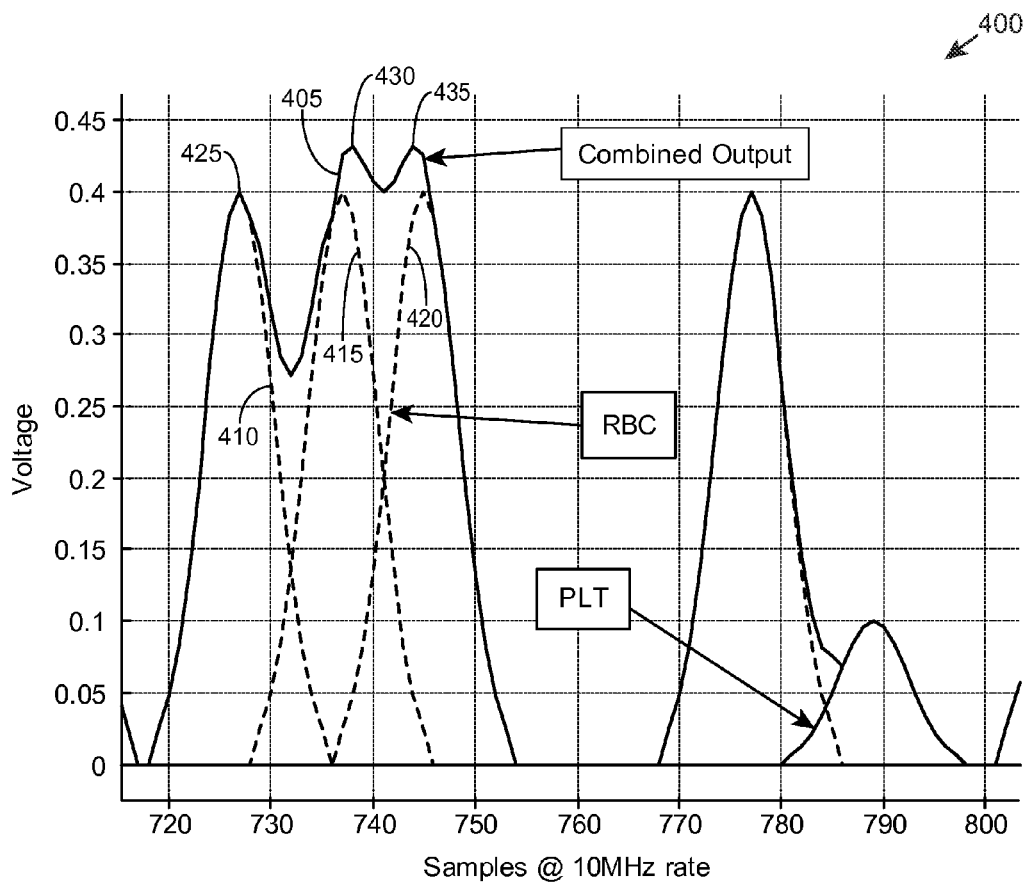
FIG. 4 illustrates a plot of a combined output response for a coincident event, along with plots of the individual sample events within the coincident event, according to one embodiment.

FIG. 4 illustrates a plot of an example set of signal data with a combined output signal for multiple sample events that are proximate to one another, according to one embodiment. The plot 400 illustrates the signal data 405 (e.g., combined output signal for multiple sample events) that is received from the analog to digital converter and which includes multiple peaks. For example, the horizontal axis shows samples taken at a sampling rate of 10 MHz. The vertical axis shows the associated voltage level for each sample. As shown, the combined output signal 405 includes a triplet of sample events 410, 415, and 420. The resulting combined output signal 405 is shown having three peaks 425, 430, and 435, which are produced from the occurrence of sample events, 410, 415, and 420. The successive cancellation module described for FIG. 3, for example, extracts the energy for these sample events successively and iteratively by cancelling the energy of the strongest signal first.

Returning to FIG. 3, if at block 316, only one peak height is found within the sample event, then the skewness of the pulse is computed, as represented by block 326. Skewness is a third order moment of the pulse, and may be used to determine whether a smaller sample event is present proximate to a larger sample event. In one embodiment, for example, skewness may be computed by the following equation.

$$\text{Skew} = \frac{n}{(n-1)(n-2)} \sum \left(\frac{x_i - \bar{x}}{s}\right)^2$$

A predetermined skewness threshold may be predetermined and used to indicate whether a smaller sample event is proximate a larger sample event. For example, if the computed skewness is greater than the predetermined threshold level (e.g., +/−0.15), then it may be determined that a smaller cell even is proximate a larger sample event, and then the successive cancellation module may be executed to subtract out the largest sample event, as represented by the arrow from block 328 to block 318. If the computed skewness is less than the predetermined threshold level, then it is determined that no smaller sample event is present, and to block 330 where the local maximum of the peak amplitude within a range (e.g., +/−0.5 microseconds) is identified for other channels of data for all the peaks found in the window. In this way, sample event data from all channels may be gathered for the sample event, as represented by block 332.

FIG. 5 illustrates an example of a positively skewed distribution 510 and a negatively skewed distribution 520. A positive or negative value of skewness indicates that a pulse has either leading or lagging trail. Leading and lagging trail is caused by any smaller cells that pass in very close proximity of a larger cell. Once the larger sample event response is subtracted as per the successive cancellation algorithm described above from the combined response, precise peak height as well as higher order moments can be computed for the smaller sample event.

FIG. 6 illustrates an example combined output of a large sample event in close proximity to a smaller sample event. As show, plot 600 illustrates signal data 610 (e.g., combined output signal for the multiple sample events) that is received from the analog to digital converter. For example, the horizontal axis shows samples taken at a sampling rate of 10 MHz. The vertical axis shows the associated voltage level for each sample. As shown, the combined output signal 610 includes a large sample event 615 (e.g., from a red blood cell, RBC) and a smaller sample event 620 (e.g., from a smaller platelet, PLT). The resulting combined output signal 610 is a larger event that is skewed on the lagging trail (on the right). Furthermore, once the stronger signal (i.e., the larger sample event) is cancelled at the right offset (e.g., time index), the weaker signal (i.e., the smaller sample event) is easily detectable.

Figure 7:
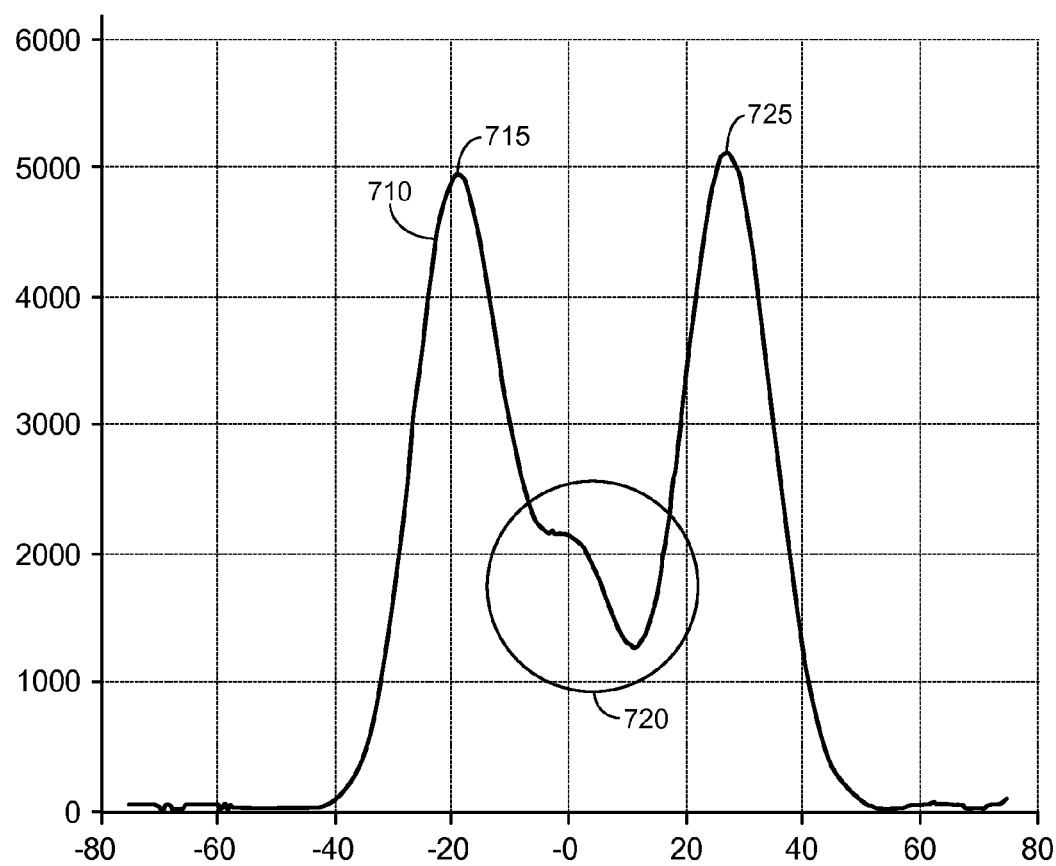
FIG. 7 illustrates a plot of a combined response for a coincident event, according to one embodiment.

FIG. 7 illustrates an example combined output signal 710 when a smaller sample event (e.g., platelet) is between two large sample events (e.g., red blood cells) and at the shoulder of the first large sample event. The large peaks 715 and 725 are indicative of the larger sample events (e.g., due to the red blood cells), and the skewness seen at 720 is indicative that a small sample event (e.g., platelet) is present.

Figure 8:
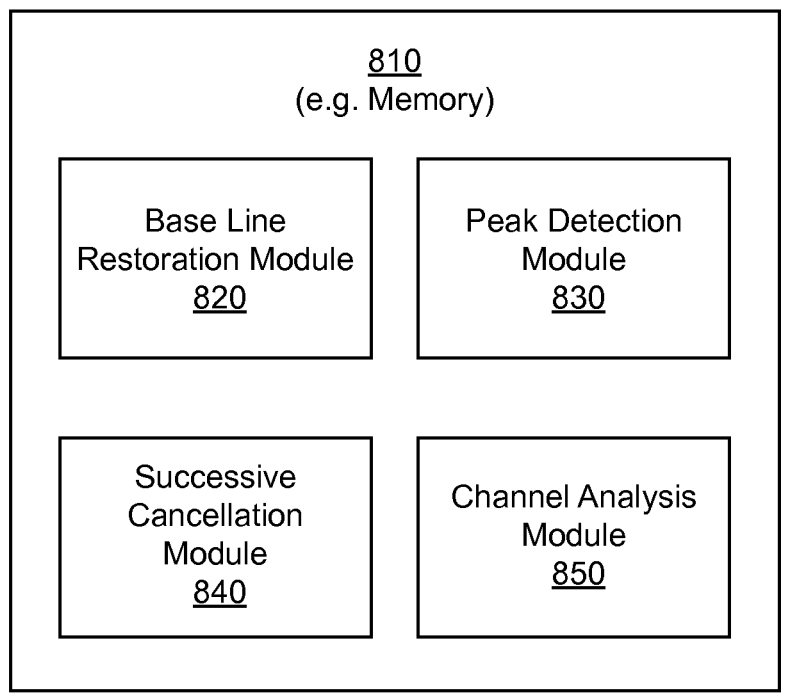
FIG. 8 illustrates a functional block diagram of a base line restoration module, peak detection module, successive cancellation module, and channel analysis module which perform the method of FIG. 3, according to one embodiment

FIG. 8 illustrates a functional block diagram of a base line restoration module, peak detection module, successive cancellation module, and channel analysis module which perform the method shown in FIG. 3, according to one embodiment. The base line restoration module 820, peak detection module 830, successive cancellation module 840, and channel analysis module 850 are shown within memory 810 and may be executed by a processing device (e.g., processor, microprocessor, application-specific integrated circuits (ASICS), programmable logic devices (PLDs), field-programmable gate arrays (FPGAs), etc.) to perform the functions as identified in the method described in FIG. 3. Memory 810 may include, for example, embedded or non-embedded memory, as well as nonvolatile or volatile memory. For instance, memory 801 may include memory 206, volatile RAM 205, ROM 207, such as shown in FIG. 2; or may be embedded in an ASIC or FPGA, etc.; or may also include, but is not limited to, non-transient machine readable mediums, such as described further below. The term processing device is used broadly herein, and may refer to one or more processor, microprocessors, application-specific integrated circuits (ASICS), programmable logic devices (PLDs), field-programmable gate arrays (FPGAs), etc., and/or any other processing device.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example.

It should be understood that some of the techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The preceding examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

That which is claimed is:

1. A method of detecting coincident sample events, comprising:
   receiving a first set of signal data representing detected signals from a flow cytometer system;
   detecting, with a peak detection module, one or more peaks within the signal data; and
   cancelling, with a successive cancellation module, one or more individual sample events from the signal data at corresponding time indexes, wherein the cancellation of more than one individual sample event is successive.

2. The method of claim 1, wherein the cancellation comprises:
   detecting a first peak event and a corresponding first time index for the first peak event;
   generating a model sample event based on a stored beam profile and height of the first peak event; and
   subtracting out energy for the model sample event from energy of the signal data at the corresponding first time index.

3. The method of claim 2, wherein multiple peaks are detected within the signal data, and wherein when the energy of the signal data is decreased by the energy of the model sample event, the cancellation steps of claim 2 are successively repeated for successive peak events and corresponding time indexes.

4. The method of claim 1, wherein energy for larger sample events are first subtracted out of energy of the signal data.

5. The method of claim 1, wherein the successive cancellation of more than one individual sample event is also iterative, wherein the iterative cancellation corrects a peak determination of a previously detected and cancelled sample event.

6. The method of claim 1, wherein only one peak is detected within the signal data, and wherein the method comprises:
   computing, with a skewness detection module, a skewness of the peak of the signal data to determine if a smaller sample event is proximate a larger sample event.

7. The method of claim 6, further comprising:
   detecting, with the skewness detection module, a skewness indicating that a smaller sample event is proximate a larger sample event;
   wherein a model sample event represents the larger sample event, and wherein an energy of the larger sample event is subtracted from an energy of the signal data at a corresponding first time index; and
   wherein a peak height and higher order moments for the smaller sample event are computed after subtraction of an energy of the model sample event from the energy of the signal data at the corresponding first time index.

8. The method of claim 1, further comprising:
   performing, with a base line restoration module, a base line restoration for the received signal data before detecting the one or more peaks, wherein the base line restoration includes:
   computing a base line restoration value based on a median value of a prior set of signal data; and
   subtracting the base line restoration value from the received signal data when the received signal data is greater than a predetermined threshold value.

9. The method of claim 1, further comprising:
   identifying, with a channel analysis module, characteristics from one or more other channels of signal data within a predetermined window of time for each of the one or more peaks detected.

10. A flow cytometer system, comprising:
    a flow cell for streaming a hydro-dynamically focused core stream past an interrogation zone;
    beam shaping optics positioned to receive and manipulate a first light beam, and to produce a resulting light beam that irradiates the core stream at the interrogation zone of the flow cell;
    a detection system to detect resulting light from the flow cell when irradiated; and
    a data processing system operably coupled to the detection system to generate and process signal data representing the resulting light detected by the detection system, wherein the processing of the signal data comprises:
    receiving a first set of signal data from the detection system;
    detecting one or more peaks within the signal data; and
    cancelling one or more individual sample events from the signal data at corresponding time indexes, wherein the cancellation of more than one individual sample event is successive.

11. The flow cytometer system of claim 10, wherein the cancellation comprises:
    detecting a first peak event and a corresponding first time index for the first peak event;
    generating a model sample event based on a stored beam profile and height of the first peak event; and
    subtracting out energy for the model sample event from energy of the signal data at the corresponding first time index.

12. The flow cytometer system of claim 11, wherein multiple peaks are detected within the signal data, and wherein when the energy of the signal data is decreased by the energy of the model sample event, the cancellation steps of claim 11 are successively repeated for successive peak events and corresponding time indexes.

13. The flow cytometer system of claim 10, wherein energy for larger sample events are first subtracted out of energy of the signal data.

14. The flow cytometer system of claim 10, wherein the successive cancellation of more than one individual sample event is also iterative, wherein the iterative cancellation corrects a peak determination of a previously detected and cancelled sample event.

15. The flow cytometer system of claim 10, wherein only one peak is detected within the signal data, and wherein the processing of the signal data further comprises:
    computing a skewness of the peak of the signal data to determine if a smaller sample event is proximate a larger sample event.

16. The flow cytometer system of claim 15, wherein the processing of the signal data further comprises:
    detecting a skewness indicating that a smaller sample event is proximate a larger sample event;
    wherein a model sample event represents the larger sample event, and wherein an energy of the larger sample event is subtracted from an energy of the signal data at a corresponding first time index; and
    wherein a peak height and higher order moments for the smaller sample event are computed after subtraction of an energy of the model sample event from the energy of the signal data at the corresponding first time index.

17. The flow cytometer system of claim 10, wherein the processing of the signal data further comprises:
    performing, with a base line restoration module, a base line restoration for the received signal data before detecting the one or more peaks, wherein the base line restoration includes:
        computing a base line restoration value based on a median value of a prior set of signal data; and
        subtracting the base line restoration value from the received signal data when the received signal data is greater than a predetermined threshold value.

18. The flow cytometer system of claim 10, wherein the processing of the signal data further comprises:
    identifying characteristics from one or more other channels of signal data within a predetermined window of time for each of the one or more peaks detected.

19. A non-transient machine-readable medium having machine-executable instructions stored thereon, which when executed by a processor, cause the processor to:
    receive a first set of signal data representing detected signals from a flow cytometer system;
    detect, with a peak detection module, one or more peaks within the signal data; and
    cancel, with a successive cancellation module, one or more individual sample events from the signal data at corresponding time indexes, wherein the cancellation of more than one individual sample event is successive.

20. The non-transient machine-readable medium of claim 19, wherein the cancellation comprises:
    detecting a first peak event and a corresponding first time index for the first peak event;
    generating a model sample event based on a stored beam profile and height of the first peak event; and
    subtracting out energy for the model sample event from energy of the signal data at the corresponding first time index.

21. The non-transient machine-readable medium of claim 20, wherein multiple peaks are detected within the signal data, and wherein when the energy of the signal data is decreased by the energy of the model sample event, the cancellation steps of claim 20 are successively repeated for successive peak events and corresponding time indexes.

22. The non-transient machine-readable medium of claim 19, wherein energy for larger sample events are first subtracted out of energy of the signal data.

23. The non-transient machine-readable medium of claim 19, wherein the successive cancellation of more than one individual sample event is also iterative, wherein the iterative cancellation corrects a peak determination of a previously detected and cancelled sample event.

24. The non-transient machine-readable medium of claim 19, wherein only one peak is detected within the signal data, and wherein the execution of the instructions by the processor, further causes the processor to:
    compute a skewness of the peak of the signal data to determine if a smaller sample event is proximate a larger sample event.

25. The non-transient machine-readable medium of claim 24, wherein the execution of the instructions by the processor, further causes the processor to:
    detect a skewness indicating that a smaller sample event is proximate a larger sample event;
    wherein a model sample event represents the larger sample event, and wherein an energy of the larger sample event is subtracted from an energy of the signal data at a corresponding first time index; and
    wherein a peak height and higher order moments for the smaller sample event are computed after subtraction of an energy of the model sample event from the energy of the signal data at the corresponding first time index.

26. The non-transient machine-readable medium of claim 19, wherein the execution of the instructions by the processor, further causes the processor to:
    perform, with a base line restoration module, a base line restoration for the received signal data before detecting the one or more peaks, wherein the base line restoration includes:
        computing a base line restoration value based on a median value of a prior set of signal data; and
        subtracting the base line restoration value from the received signal data when the received signal data is greater than a predetermined threshold value.

27. The non-transient machine-readable medium of claim 19, wherein the execution of the instructions by the processor, further causes the processor to:
    identify characteristics from one or more other channels of signal data within a predetermined window of time for each of the one or more peaks detected.

28. A data processing system, comprising:
    a processor;

memory operably coupled to the processor, wherein the memory includes executable instructions stored thereon, which when executed by the processor, cause the processor to:

receive a first set of signal data representing detected signals from a flow cytometer system;

detect, with a peak detection module, one or more peaks within the signal data; and cancel, with a successive cancellation module, one or more individual sample events from the signal data at corresponding time indexes, wherein the cancellation of more than one individual sample event is successive.

29. The data processing system of claim 28, wherein the cancellation comprises:

detecting a first peak event and a corresponding first time index for the first peak event;

generating a model sample event based on a stored beam profile and height of the first peak event; and subtracting out energy for the model sample event from energy of the signal data at the corresponding first time index.

30. The data processing system of claim 29, wherein multiple peaks are detected within the signal data, and wherein when the energy of the signal data is decreased by the energy of the model sample event, the cancellation steps of claim 29 are successively repeated for successive peak events and corresponding time indexes.

31. The data processing system of claim 28, wherein energy for larger sample events are first subtracted out of energy of the signal data.

32. The data processing system of claim 28, wherein the successive cancellation of more than one individual sample event is also iterative, wherein the iterative cancellation corrects a peak determination of a previously detected and cancelled sample event.

33. The data processing system of claim 28, wherein only one peak is detected within the signal data, and wherein the execution of the instructions by the processor, further causes the processor to:

compute a skewness of the peak of the signal data to determine if a smaller sample event is proximate a larger sample event.

34. The data processing system of claim 33, wherein the execution of the instructions by the processor, further causes the processor to:

detect a skewness indicating that a smaller sample event is proximate a larger sample event;

wherein a model sample event represents the larger sample event, and wherein an energy of the larger sample event is subtracted from an energy of the signal data at a corresponding first time index; and wherein a peak height and higher order moments for the smaller sample event are computed after subtraction of an energy of the model sample event from the energy of the signal data at the corresponding first time index.

35. The data processing system of claim 28, wherein the execution of the instructions by the processor, further causes the processor to:

perform, with a base line restoration module, a base line restoration for the received signal data before detecting the one or more peaks, wherein the base line restoration includes:

computing a base line restoration value based on a median value of a prior set of signal data; and subtracting the base line restoration value from the received signal data when the received signal data is greater than a predetermined threshold value.

36. The data processing system of claim 28, wherein the execution of the instructions by the processor, further causes the processor to:

identify characteristics from one or more other channels of signal data within a predetermined window of time for each of the one or more peaks detected.

37. The data processing system of claim 28, wherein the data processing system comprises programmable circuitry, and the processor and memory are modules embedded within the programmable circuitry.

* * * * *